(12) United States Patent
Findlay et al.

(10) Patent No.: US 6,903,208 B2
(45) Date of Patent: Jun. 7, 2005

(54) POLYMERS AND THEIR USE

(75) Inventors: Paul Hugh Findlay, Wirral (GB); Christopher Clarkson Jones, Wirral (GB); Dax Kukulj, Kingston (AU)

(73) Assignee: Unilever Home & Personal Care USA Division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/225,863

(22) Filed: Aug. 22, 2002

(65) Prior Publication Data

US 2003/0162688 A1 Aug. 28, 2003

(30) Foreign Application Priority Data

Aug. 31, 2001 (GB) ............................................. 0121148

(51) Int. Cl.⁷ ............................ C08B 37/00; C11D 3/00
(52) U.S. Cl. .................. 536/55.1; 536/53; 536/116; 536/120; 510/470; 510/471; 510/473; 510/515
(58) Field of Search ........................... 536/53, 116, 120, 536/55.1, 56, 123.1; 510/515, 470, 471, 473

(56) References Cited

U.S. PATENT DOCUMENTS

| | | | |
|---|---|---|---|
| 4,454,295 A | | 6/1984 | Wittmann et al. |
| 5,082,914 A | * | 1/1992 | Cook et al. .................. 527/300 |
| 5,730,760 A | | 3/1998 | Kirk et al. |
| 6,066,727 A | | 5/2000 | Yamamoto et al. |

FOREIGN PATENT DOCUMENTS

| | | | | |
|---|---|---|---|---|
| EP | 0366237 | | 8/1989 | |
| EP | 0 459 821 A2 | | 5/1991 | |
| EP | 1095959 | | 10/2000 | |
| GB | 671721 | | 5/1952 | |
| GB | 1031484 | | 6/1966 | |
| GB | 1 549 180 | | 7/1979 | |
| JP | 09136901 | * | 5/1997 | ............. C08B/3/14 |
| WO | 92/13114 | | 8/1992 | |
| WO | 95/35087 | | 12/1995 | |
| WO | 98/00500 | | 1/1998 | |
| WO | 98/29528 | | 7/1998 | |
| WO | 99/14245 | | 3/1999 | |
| WO | 99/14295 | | 3/1999 | |
| WO | 99/21892 | | 5/1999 | |
| WO | WO 00/18861 | * | 4/2000 | ............. C11D/3/22 |

OTHER PUBLICATIONS

International Search Report PCT/EP 02 09227 mailed Dec. 16, 2002, 3 pp. Patent Abstracts of Japan, vol. 1997, No. 9 (May 27, 1997) Abstract of JP 09136901—1 p.
UK Search Report GB 0121148.1 mailed Mar. 8, 2002, 2 pp.
Chem. Abstracts 133:239476 & JP 2000256613 (Shin–Etsu Chemical Industry Co.).
Abstracts of JP 6248002 (Natoko Paint KK).
Abstracts of JP 11107191 (Toppan Printing Co.).
Abstracts of JP 09136901 (Shin–Etsu Chemical Co.) (Previously Submitted).

* cited by examiner

Primary Examiner—James O. Wilson
Assistant Examiner—Ganapathy Krishnan
(74) Attorney, Agent, or Firm—Alan A. Bornstein

(57) ABSTRACT

A substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

22 Claims, No Drawings

POLYMERS AND THEIR USE

TECHNICAL FIELD

The present invention relates to a substituted polysaccharide of the kind comprising a benefit agent and a deposition aid for deposition of the benefit agent onto a substrate. It further relates to a method of depositing a benefit agent from solution or dispersion, onto a substrate.

BACKGROUND OF THE INVENTION

The deposition of a benefit agent onto a substrate, such as a fabric, is well known in the art. In laundry applications typical "benefit agents" include fabric softeners and conditioners, soil release polymers, sunscreens; and the like. Deposition of a benefit agent is used, for example, in fabric treatment processes such as fabric softening to impart desirable properties to the fabric substrate.

Conventionally, the deposition of the benefit agent has had to rely upon the attractive forces between the oppositely charged substrate and the benefit agent. Typically this requires the addition of benefit agents during the rinsing step of a treatment process so as to avoid adverse effects from other charged chemical species present in the treatment compositions. For example, cationic fabric conditioners are incompatible with anionic surfactants in laundry washing compositions.

Such adverse charge considerations can place severe limitations upon the inclusion of benefit agents in compositions where an active component thereof is of an opposite charge to that of the benefit agent. For example, cotton is negatively charged and thus requires a positively charged benefit agent in order for the benefit agent to be substantive to the cotton, i.e. to have an affinity for the cotton so as to absorb onto it.

Often the substantivity of the benefit agent is reduced and/or the deposition rate of the material is reduced because of the presence of incompatible charged species in the compositions. However, in recent times, it has been proposed to deliver a benefit agent in a form whereby it is substituted onto another chemical moiety which increases its affinity for the substrate in question.

PRIOR ART

WO-A-98/00500 discloses detergent compositions comprising a peptide or protein deposition aid having a high affinity for fibres or a surface, and a benefit agent attached/adsorbed to the deposition aid. However, this deposition aid does not change chemically such as to increase its affinity for the substrate during the treatment process.

GB-A-1 031 484 discloses stable aqueous dispersions of elastic copolymers which can be converted to cross-linked polymers by the action of heat or acid. They can be used to produce films or covering layers. However, none of the compounds has a benefit agent attached to the deposition enhancing part. There is no disclosure of using these materials in methods of laundry or fabric care.

U.S. Pat. No. 5,730,760 discloses a process of fabric washing in which a dye redeposition inhibiting agent is used. The dye redeposition inhibiting polymer used is of a specific type, being produced by polymerising, for example, vinylester monomers. There is not any mention of materials having any surface substantive properties nor is there a description of any reaction by which such surface substantive properties increase during use.

WO-A-92/13114 discloses hair fixative polymers which form a film after application. The polymers are fundamentally different from those of the present invention in that they do not comprise a deposition part attached to a benefit agent. The polymeric material has no particular affinity for hair—it is just applied onto it. There is certainly no mention of a reaction which increases the affinity. Any reaction which occurs leads to the cross-linking of polymer and the formation of film. It is not disclosed that the polymers should be water-soluble of dispersible—they are normally dissolved in an inert carrier such as alcohol.

WO-A-95/35087 discloses a hair fixative amphoteric polymer composition. It is insoluble in water but can be solubilised by use of neutralisers or solubilising alcohol/water mixtures. The polymers do not to undergo any reaction which increases their affinity for hair. There is no benefit agent attached to the polymer.

WO-A-98/29528 discloses cellulose ethers in which some substituents are (poly)alkoxylated, analogues of the latter in which the (poly)alkoxylated groups are terminated with a cationic moiety in the form of a quaternary ammonium group, and cellulose ethers in which some substituents are carboxylic acids in the salt form (i.e. the materials are essentially carboxymethylcellulose variants). None of these substituents in any variant is of a kind which would undergo a chemical change to enhance fabric affinity.

WO-A-99/14245 discloses laundry detergent compositions containing cellulosic based polymers to provide appearance and integrity benefits to fabrics. These polymers are cellulosic polymers in which the saccharide rings have pendant oxygen atoms to which substituents 'R' are bonded, i.e. they are attached to the rings via an ether linkage. The groups 'R' can be hydrogen, lower alkyl or alkylene linkages terminated by carboxylic acid, ester or amide groups. Optionally, up to five alkyleneoxy groups may be interspersed between the groups are the respective oxygen atom. None of the pendant groups is a benefit agent group. However, at least some of these groups may undergo a chemical change such as hydrolysis, in the wash liquor. However no such change would result in an increased affinity for the fabric. On the contrary, because the "ester" group is configured with the carbonyl group closer to the polysaccharide than the oxygen atom (i.e. esters of carboxyalkyl groups), any hydrolysis will result in free acid substituents which will actually result in an increase in solubility and therefore, a decrease in affinity for the fabric.

WO-A-99/14295 discloses structures analogous to those described in WO-A-99/14245 but in one alternative, the substituents 'R' together with the oxygen on the saccharide ring, constitute pendant half-esters of certain dicarboxylic acids. A single example of such a material is given. Again, no pendant group is a benefit agent group. However, the dicarboxylic acid half-esters would tend to hydrolyse in the wash liquor and thereby increase affinity of the material for a cotton fabric. However, first, this mechanism of action or behaviour is not mentioned. Second, the hydrolysis rate of such dicarboxylic acids half esters is not as great as that of esters of monocarboxylic acids (which are not disclosed or claimed in WO-A-99/14295). Third, the degree of substitution for this variant is specified as being from 0.001 to 0.1. This is so low as to make the enhancement of fabric affinity too low to be worthwhile for this mechanism of action. Fourth, the structures described and claimed insofar as they have such half ester substituents, must also have substituents of the type which are carboxyalkyl groups or esters thereof, i.e. of the type also described in WO-A-99/14245. In the latter (ester) case, these would hydrolyse to the free acid form. The degree of substitution of the latter (0.2 to 2) is considerably higher than for the half-ester groups and the resultant increase in solubility would easily negate any enhanced affinity for the fabric by hydrolysis of the half-ester groups.

WO-A-00/18861 provides a water-soluble or water-dispersible material for deposition onto a substrate during a treatment process, wherein the material comprises:
  (i) a deposition enhancing part having a polymeric backbone; and
  (ii) a benefit agent group attached to the deposition enhancing part by a hydrolytically stable bond;
such that the material undergoes during the treatment process, a chemical change which does not involve the hydrolytically stable bond and by which change the affinity of the material onto the substrate is increased. The preferred materials are substituted polysaccharides.

WO-A-00/18861 mentions as possible benefit groups, lubricants, ironing aids and fabric softeners. However, it is known that silicone materials are especially useful agents for delivering this kind of benefit. Up to now, there has been no specific teaching of how to deliver a silicone to a cotton substrate by use of a polysaccharide. The present invention is aimed at solving this problem.

DEFINITION OF THE INVENTION

A first aspect of the present invention provides a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

A second aspect of the present invention provides a method for depositing a silicone onto a substrate, the method comprising, contacting in an aqueous medium, the substrate and a substituted polysaccharide according to the first aspect of the invention.

A third aspect of the present invention also provides compositions comprising a material according to the first aspect of the present invention. In particular, such compositions preferably comprise one or more surfactants and are suitable for use in washing applications such as laundry.

A further aspect of the invention provides the use of a composition according to the third aspect to enhance the softening benefit of the composition on a substrate.

DETAILED DESCRIPTION OF THE INVENTION

The Substituted Polysaccharide

In the substituted polysaccharide, the silicone chain is preferably attached to the polysaccharide by a covalent stable bond. That means that the bonding of the silicone should be sufficiently stable so as not to undergo hydrolysis in the environment of the treatment process for the duration of that process. For example, in laundry cleaning applications, the substituted polysaccharide should be sufficiently stable so that the bond between the silicone and polysaccharide does not undergo hydrolysis in the wash liquor, at the wash temperature, before the silicone has been deposited onto the fabric.

Preferably, the bond between the silicone and the polysaccharide is such that the decay rate constant ($k_d$) of the material in an aqueous solution at 0.01 wt % of the material together with 0.1 wt % of anionic surfactant at a temperature of 40° C. at a pH of 10.5 is such that $k_d < 10^{-3} s^{-1}$.

The substituted polysaccharide of the present invention is water-soluble or water-dispersible in nature and comprises a polysaccharide substituted with at least one silicone attached to the polysaccharide aid by a hydrolytically stable bond.

By water-soluble, as used herein, what is meant is that the material forms an isotropic solution on addition to water or another aqueous solution.

By water-dispersible, as used herein, what is meant is that the material forms a finely divided suspension on addition to water or another aqueous solution.

By an increase in the affinity of the substituted polysaccharide for a substrate such as a textile fabric upon a chemical change, what is meant is that at some time during the treatment process, the amount of material that has been deposited is greater when the chemical change is occurring or has occurred, compared to when the chemical change has not occurred and is not occurring, or is occurring more slowly, the comparison being made with all conditions being equal except for that change in the conditions which is necessary to affect the rate of chemical change.

Deposition onto a substrate includes deposition by adsorption, co-crystallisation, entrapment and/or adhesion.

The Polysaccharide Part

The polysaccharide is preferably $\beta_{1-4}$ linked and is a cellulose, a cellulose derivative, or another $\beta_{-1,4}$-linked polysaccharide having an affinity for cellulose, such as mannan and glucomannan.

Preferably, the polysaccharide has only $\beta_{-1,4}$ linkages. Optionally, the polysaccharide has linkages in addition to the $\beta_{-1,4}$ linkages, such as $\beta_{-1,3}$ linkages. Thus, optionally some other linkages are present. Polysaccharide backbones which include some material which is not a saccharide ring are also within the ambit of the present invention (whether terminal or within the polysaccharide chain).

The polysaccharide may be straight or branched. Many naturally occurring polysaccharides have at least some degree of branching, or at any rate at least some saccharide rings are in the form of pendant side groups (which are therefore not in themselves counted in determining the degree of substitution) on a main polysaccharide backbone.

A polysaccharide comprises a plurality of saccharide rings which have pendant hydroxyl groups. In the substituted polysaccharides of the present invention, at least some of these hydroxyl groups are independently substituted by, or replaced with, one or more other substituents, at least one being a silicone chain. The "average degree of substitution" for a given class of substituent means the average number of substituents of that class per saccharide ring for the totality of polysaccharide molecules in the sample and is determined for all saccharide rings.

The Deposition Enhancing Group

A deposition enhancing group is a group which undergoes a chemical change in use, and is attached to the polysaccharide agent group by means of a covalent stable bond. This chemical change results in an increase of the affinity of the material for the substrate and is referred to further below.

The chemical change which causes the increased substrate affinity is preferably caused by hydrolysis, perhydrolysis or bond-cleavage, optionally catalysed by an enzyme or another catalyst. Hydrolysis of substituent ester-linked groups is typical.

By ester linkage is meant that the hydrogen of an —OH group has been replaced by a substituent such as R'—CO—, R'SO$_2$— etc to form a carboxylic acid ester, sulphonic acid ester (as appropriate) etc together with the remnant oxygen attached to the saccharide ring. In some cases, the group R' may for example contain a heteroatom, e.g. as an —NH— group attached to the carbonyl, sulphonyl etc group, so that the linkage as a whole could be regarded as a urethane etc linkage. However, the term ester linkage is still to be construed as encompassing these structures.

The average degree of substitution of these pendant groups which undergo the chemical change is preferably from 0.1 to 3 (e.g. from 0.3 to 3), more preferably from 0.1 to 1 (e.g. from 0.3 to 1).

The Silicone Chain(s)

As used herein the term "silicone chain" means a polysiloxane or derivative thereof. In the section "Preferred Overall Structure" hereinbelow, various preferred silicone chains are recited and these are typically suitable, whether or not the substituted polysaccharide conforms to the preferred overall structure.

Preferred Overall Structures

Preferred substituted polysaccharides of the invention are cellulosic polymers of formula (I):

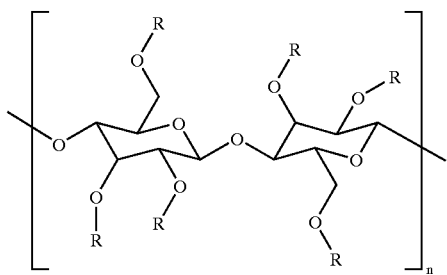

(optional β-$_{1,3}$ and/or other linkages and/or other groups being permitted in the above formula (I))wherein at least one or more —OR groups of the polymer are substituted by or replaced by independently selected silicone chains and at least one or more R groups are independently selected from groups of formula:

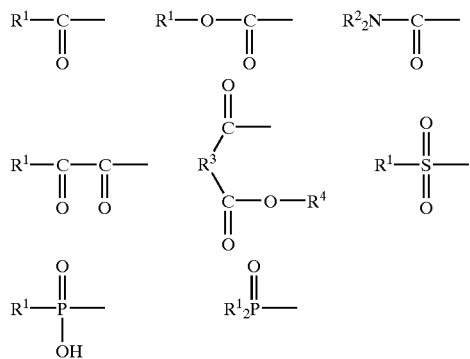

wherein each $R^1$ is independently selected from $C_{1-20}$ (preferably $C_{1-6}$) alkyl, $C_{2-20}$ (preferably $C_{2-6}$) alkenyl (e.g. vinyl) and $C_{5-7}$ aryl (e.g. phenyl) any of which is optionally substituted by one or more substituents independently selected from $C_{1-4}$ alkyl, $C_{1-12}$ (preferably $C_{1-4}$) alkoxy, hydroxyl, vinyl and phenyl groups;

each $R^2$ is independently selected from hydrogen and groups $R^1$ as hereinbefore defined;

$R^3$ is a bond or is selected from $C_{1-4}$ alkylene, $C_{2-4}$ alkenylene and $C_{5-7}$ arylene (e.g. phenylene) groups, the carbon atoms in any of these being optionally substituted by one or more substituents independently selected from $C_{1-12}$ (preferably $C_{1-4}$) alkoxy, vinyl, hydroxyl, halo and amine groups;

each $R^4$ is independently selected from hydrogen, counter cations such as alkali metal (preferably Na) or ½ Ca or ½ Mg, and groups $R^1$ as hereinbefore defined; and groups R which together with the oxygen atom forming the linkage to the respective saccharide ring forms an ester or hemi-ester group of a tricarboxylic- or higher polycarboxylic- or other complex acid such as citric acid, an amino acid, a synthetic amino acid analogue or a protein;

any remaining R groups being selected from hydrogen and other substituents.

For the avoidance of doubt, as already mentioned, formula (I), some of the R groups may optionally have one or more structures, for example as hereinbefore described. For example, one or more R groups may simply be hydrogen or an alkyl group.

Preferred groups which undergo the chemical change may for example be independently selected from one or more of acetate, propanoate, trifluroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Particularly preferred such groups are the monoacetate, hemisuccinate, and 2-(2-hydroxy-1-oxopropoxy) propanoate. The term "monoacetate" is used herein to denote those acetates with the degree of substitution of 1 or less on a cellulose or other β-1,4 polysaccharide backbone.

Cellulose esters of hydroxyacids can be obtained using the acid anhydride in acetic acid solution at 20–30° C. and in any case below 50° C. When the product has dissolved the liquid is poured into water (b.p. 316, 160). Tri-esters can be converted to secondary products as with the triacetate. Glycollic and lactic ester are most common.

Cellulose glycollate may also be obtained from cellulose chloracetate (GB-A-320 842) by treating 100 parts with 32 parts of NaOH in alcohol added in small portions.

An alternative method of preparing cellulose esters consists in the partial displacement of the acid radical in a cellulose ester by treatment with another acid of higher ionisation constant (FR-A-702 116). The ester is heated at about 100° C. with the acid which, preferably, should be a solvent for the ester. By this means cellulose acetate-oxalate, tartrate, maleate, pyruvate, salicylate and phenylglycollate have been obtained, and from cellulose tribenzoate a cellulose benzoate-pyruvate. A cellulose acetate-lactate or acetate-glycollate could be made in this way also. As an example cellulose acetate (10 g.) in dioxan (75 ml.) containing oxalic acid (10 g.) is heated at 100° C. for 2 hours under reflux.

Multiple esters are prepared by variations of this process. A simple ester of cellulose, e.g. the acetate, is dissolved in a mixture of two (or three) organic acids, each of which has an ionisation constant greater than that of acetic acid (1.82× $10^{-5}$): With solid acids suitable solvents such as propionic acid, dioxan and ethylene dichloride are used. If a mixed cellulose ester is treated with an acid this should have an ionisation constant greater than that of either of the acids already in combination.

A cellulose acetate-lactate-pyruvate is prepared from cellulose acetate, 40 per cent. acetyl (100 g.), in a bath of 125 ml. pyruvic acid and 125 ml. of 85 per cent. lactic acid by heating at 100° C. for 18 hours. The product is soluble in water and is precipitated and washed with ether-acetone. M.p. 230–250° C.

In the case of those materials having a cellulose backbone and pendant ester groups, without being bound by any particular theory or explanation, the inventors have conjectured that the mechanism of deposition is as follows.

Cellulose is substantially insoluble in water. Attachment of the ester groups to make a cellulose derivative causes disruption of the hydrogen bonding between rings of the cellulose chain or chains, thus increasing water solubility or dispersibility. In the treatment liquor, the ester groups are hydrolysed, causing the cellulose derivative to increase its affinity for the substrate, e.g. the fabric.

In the case when solubilising groups are attached to the polysaccharide, this is typically via covalent bonding and, may be pendant upon the backbone or incorporated therein. The type of solubilising group may alter according to where the group is positioned with respect to the backbone.

In this specification the "n" subscript used in the general formulae of the substituted polysaccharide is a generic reference to a polymer. Although "n" can also mean the actual (average) number of repeat units present in the polysaccharide, it is more meaningful to refer to "n" by the number average molecular weight.

The number average molecular weight ($M_n$) of the substituted polysaccharide part may typically be in the range of 1,000 to 200,000, for example 2,000 to 100,000, e.g. as measured using GPC with multiple angle laser scattering detection.

The silicone chains preferred for use to substitute or replace (dependent upon the synthetic route use to prepare the substituted polysaccharides of the invention) at least one —OR group in the compounds of formula (I) are representative of preferred silicone chains for use in substituted polysaccharides used in the invention as a whole, ie whether or not the overall structure conforms to Formula (I).

Preferably, the average degree of substitution for the silicone chains is from 0.001 to 0.5, preferably 0.01 to 0.5, more preferably from 0.01 to 0.1, still more preferably from 0.01 to 0.05.

Even more preferably the average degree of substitution for the silicone chains is from 0.00001 to 0.1, more preferably from 0.001 to 0.04, even more preferably from 0.001 to 0.01.

Preferred silicone chains suitable for this use are those of formula:

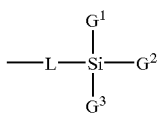

wherein L is absent or is a linking group and one or two of substituents $G^1$–$G^3$ is a methyl group, the remainder being selected from groups of formula

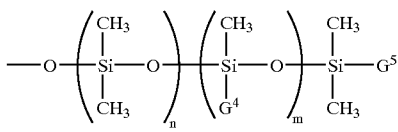

the —Si(CH$_3$)$_2$O— groups and the —Si(CH$_3$O)(G$^4$)— groups being arranged in random or block fashion, but preferably random.

wherein n is from 5 to 1000, preferably from 10 to 200 and m is from 0 to 100, preferably from 0 to 20, for example from 1 to 20.

$G^4$ is selected from groups of formula:
—(CH$_2$)$_p$—CH$_3$, where p is from 1 to 18
—(CH$_2$)$_q$—NH—(CH$_2$)$_r$, —NH$_2$ where q and r are independently from 1 to 3
—(CH$_2$)$_s$—NH$_2$, where s is from 1 to 3

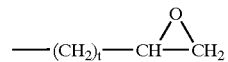

where t is from 1 to 3
—(CH$_2$)$_u$—COOH, where u is from 1 to 10,

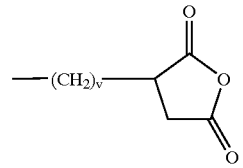

where v is from 1 to 10, and
—(CH$_2$CH$_2$O)$_w$—(CH$_2$)$_x$H, where w is from 1 to 150, preferably from 10 to 20 and x is from 0 to 10;
and $G^5$ is independently selected from hydrogen, groups defined above for $G^4$, —OH, —CH$_3$ and —C(CH$_3$)$_3$.

Other Substituents

As well as the silicone chain(s) and the pendant group(s) which undergo a chemical change to enhance deposition, pendant groups of other types may optionally be present, i.e. groups which do not confer a benefit and which do not undergo a chemical change to enhance substrate affinity. Within that class of other groups is the sub-class of groups for enhancing the solubility of the material (e.g. groups which are, or contain one or more free carboxylic acid/salt and/or sulphonic acid/salt and/or sulphate groups).

Examples of solubility enhancing substituents include carboxyl, sulphonyl, hydroxyl, (poly)ethyleneoxy- and/or (poly)propyleneoxy-containing groups, as well as amine groups.

The other pendant groups preferably comprise from 0% to 65%, more preferably from 0% to 10% of the total number of pendant groups. The water-solubilising groups could comprise from 0% to 100% of those other groups but preferably from 0% to 20%, more preferably from 0% to 10%, still more preferably from 0% to 5% of the total number of other pendant groups.

Synthetic Routes

As described above, preferred substituted polysaccharides of the present invention are those of formula (I). Further, preferred silicone chains, whether for the compounds of formula (I) or any other substituted polysaccharides of the invention are preferably attached via a linking group "-L-". This linking group is the residue of the reactants-used to form the substituted polysaccharide.

The substituted polysaccharides of the invention can be made thus:

(a) a polysaccharide is first substituted with one or more deposition enhancing groups; and
(b) one or more silicone groups are then attached.

If any other substituents are to be present, these may already be present in the commercially available polysaccharide, or attached before or after step (a) and/or (b).

Whilst steps (a) and (b) can be reversed, the reaction whereby step (a) is conducted first is preferred.

The deposition enhancing group(s) is/or are attached in step (a) according to the methodology described in WO-A-00/18861.

In step (b), one or more hydroxyl groups on the polysaccharide are reacted with a reactive group attached to the silicone chain, or the hydroxyl group(s) in question is/are converted to another group capable of reaction with a reactive group attached to the silicone chain. Listed below, are suitable mutually reactive groups. In the case of hydroxyl groups, these may be the original hydroxyl group of the polysaccharide. However, either of a pair of these mutually reactive groups may be present on the polysaccharide and the other attached to the silicone chain, or vice versa, the reaction chemistry being chosen appropriately. In the following description, for convenience, "PSC" refers to the polysaccharide chain with or without deposition enhancing group(s) and/or other substituent(s) already attached. "SXC" refers to the group $$-\underset{\underset{G^3}{|}}{\overset{\overset{G^1}{|}}{Si}}-G^2$$

as hereinbefore defined.

Preferred linking groups -L- are selected from the following, wherein preferably, the left hand end of the group depicted is connected to the saccharide ring either direct or via the residual oxygen of one of the original saccharide —OH groups and the right hand end is connected to the moiety —Si($G^1G^2G^3$). Thus, the configuration as written is PSC-L-SXC. However, the reverse configuration SXC-L-PSC is also within the ambit of this definition and this is also mentioned where appropriate.

Preferred linking groups -L- are selected from amide, ester, ether, urethane, triazine, carbonate, amine and ester-alkylene linkages.

A preferred amide linkage is:

$$-G^6-\overset{\overset{O}{\|}}{C}-\underset{\underset{G^8}{|}}{N}-G^7-$$

where $G^6$ and $G^7$ are each optionally present and are independently selected spacer groups, e.g. selected from $C_{1-14}$ alkylene groups, arylene, $C_{1-4}$ alkoxylene, a residue of an oligo- or poly-ethylene oxide moiety, $C_{1-4}$ alkylamine or a polyamine groups and
$G^8$ is hydrogen or $C_{1-4}$ alkyl.

This linkage can be formed by reacting $$PSC-G^6-\overset{\overset{O}{\|}}{C}-\underset{\underset{G^8}{|}}{N}-G^7-\underset{\underset{G^9}{|}}{NH}$$

wherein $G^7$ and $G^8$ are as hereinbefore defined and $G^9$ is hydrogen or $C_{1-4}$ alkyl; with a compound of formula:

$$SXC-G^6-\overset{\overset{O}{\|}}{C}-G^{11}$$

wherein $G^{11}$ is hydroxy, a group with active ester functionality halo, or a leaving group suitable for neucleophilie displacement such as imidazole or an imidazole-containing group and wherein $G^6$ is hereinbefore defined above, or —CO-$G^{11}$ is replaced by a cyclic acid anhydride. Active ester synthesis is described in M. Bodanszky, "The Peptides", Vol. 1, Academic Press Inc., 1975, pp105 ff.

The reverse configuration linkage may be formed by reacting $$PSC-G^{12}-\overset{\overset{O}{\|}}{C}-G^{11}$$

wherein $G^{12}$ is a ring-opened carboxylic acid anhydride, phenylene, or a group of formula or and $G^{11}$ is as hereinbefore defined;
with the group of formula $$SXC-G^6-\underset{\underset{G^8}{|}}{NH}$$

where $G^6$ and $G^8$ are as hereinbefore defined.

A preferred ester linkage has the formula $$-G^6-\overset{\overset{O}{\|}}{C}-O-G^7-$$

wherein $G^6$ and $G^7$ are as hereinbefore defined, $G^8$ optionally being absent.

This may be formed by reacting $$PSC-G^{12}-\overset{\overset{O}{\|}}{C}-G^{11}$$

wherein $G^{11}$ and $G^{12}$ are as hereinbefore defined with

SXC-$G^6$-OH wherein $G^6$ is as hereinbefore defined.

The reverse ester linkage formation may be formed by reacting

PSC-$G^7$-OH (i.e. the optionally modified polysacharide with at least one residual —OH group) with $$SXC-G^6-\overset{\overset{O}{\|}}{C}-G^{11}$$

wherein $G^6$ and $G^{11}$ are as hereinbefore defined, or —CO-$G^{11}$ may be replaced by a cyclic anhydride.

Preferred ether linkages have the formula

-$G^6$-O-$G^7$- wherein $G^6$ and $G^7$ are as hereinbefore defined, optionally one being absent.

This linkage may be formed by reacting

PSC-$G^6$-OH with $$SXC-G^{15}-\triangleleft^O$$

wherein $G^{15}$ is $C_{1-4}$ alkylene and $G^6$ is optionally absent and is as hereinbefore defined.

A preferred urethane linkage is $$-G^6-O-\underset{\underset{H}{|}}{\overset{\overset{O}{\|}}{C}}-N-G^7-$$

wherein $G^6$ and $G^7$ are as hereinbefore defined, $G^6$ optionally being absent (preferably absent in the configuration PSC-L-SXC)

PSC-G$^6$-OH

SXC-G$^7$-NCO with
wherein $G^6$ and $G^7$ are as hereinbefore defined, $G^6$ optionally being absent (preferably absent in the configuration PSC-L-SXC)

The reverse configuration is also possible but the simplest arrangement is PSC-L-SXC and wherein $G^6$ is absent. Also most common is when $G^7$ is alkylene.

The latter compound is made by reacting

SXC-G$^7$-NH$_2$ wherein $G^7$ is as hereinbefore defined;
with phosgene.

Another route is to react

PSC-G$^6$-OH wherein $G^6$ is as hereinbefore defined
with carbonyl dimidazole to form $$PSC-\overset{\overset{O}{\|}}{C}-N\underset{\diagdown}{\diagup}\hspace{-0.5em}\underset{N}{\phantom{|}}$$

and react that product with

SXC-G$^7$-NH$_2$ wherein $G^7$ is as hereinbefore defined.
Preferred triazine linkages have the formula $$-G^6-O-\underset{\underset{\underset{Cl}{|}}{\diagdown}}{\overset{\diagup N \diagdown}{\phantom{|}}}-G^7-$$

wherein $G^6$ and $G^7$ are as hereinbefore defined, $G^6$ optionally being absent.

These linkages may be formed by reacting

SXC-G$^7$-OH or

SXC-G$^7$-NH$_2$ wherein $G^7$ is as hereinbefore defined with cyanuic chloride and then with

PSC-G$^6$-OH wherein $G^6$ is as hereinbefore defined but may be absent; or (reverse -L-) by reacting

PSC-G$^7$-OH with cyanuric chloride (when $G^7$ is as hereinbefore defined) and then with

SXC-G$^6$-OH or

SXC-G$^6$-NH$_2$

Preferred carbonate linkages have the formula $$-O-\overset{\overset{O}{\|}}{C}-O-G^6-$$

wherein $G^6$ is as hereinbefore defined.
This linkage may be formed by reacting

PSC—OH with

SXC-G$^6$-OH in the presence of carbonyl dimidazole or phosgene
Preferred amine linkages have the formula $$-G^6-\overset{\overset{O}{\|}}{C}-\underset{\underset{G^8}{|}}{N}-G^7-\underset{\underset{G^9}{|}}{N}-\diagdown\underset{OH}{\diagup}G^{15}-$$

wherein $G^6$, $G^7$, $G^8$, $G^9$ and $G^{15}$ are as hereinbefore defined.
This linkage may be formed by reacting $$PSC-G^6-\overset{\overset{O}{\|}}{C}-\underset{\underset{G^8}{|}}{N}-G^7-\underset{\underset{G^9}{|}}{NH}$$

wherein $G^6$–$G^9$ are hereinbefore defined;
with $$O\triangleright-G^{15}-SXC$$

wherein $G^{15}$ is as hereinbefore defined.
Preferred ester-alkylene linkages have the formula $$-O-\overset{\overset{O}{\|}}{C}-G^6-\left(\underset{H_2}{C}\right)_2-CH_3$$

wherein $G^7$ is as hereinbefore defined.
These linkages may be prepared by reacting

PSC—OH with

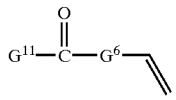

and then reacting with a hydrogen-terminated silicone chain compound (i.e. $G^5$=H) over a platinum catalyst.

Compositions

The substituted polysaccharide according to the first aspect of the present invention may be incorporated into compositions containing only a diluent (which may comprise solid and/or liquid) and/or also comprising an active ingredient. The compound is typically included in said compositions at levels of from 0.01% to 25% by weight, preferably from 0.1% to 10%, most preferably from 0.5% to 3%.

The active ingredient in the compositions is preferably a surface active agent or a fabric conditioning agent. More than one active ingredient may be included. For some applications a mixture of active ingredients may be used.

The compositions of the invention may be in any physical form e.g. a solid such as a powder or granules, a tablet, a solid bar, a paste, gel or liquid, especially, an aqueous based liquid. In particular the compositions may be used in laundry compositions, especially in liquid, powder or tablet laundry composition. The compositions of the present invention are preferably laundry compositions, especially main wash (fabric washing) compositions or rinse-added softening compositions. The main wash compositions may include a fabric softening agent and rinse-added fabric softening compositions may include surface-active compounds, particularly non-ionic surface-active compounds, if appropriate.

The detergent compositions of the invention may contain a surface-active compound (surfactant) which may be chosen from soap and non-soap anionic, cationic, non-ionic, amphoteric and zwitterionic surface-active compounds and mixtures thereof. Many suitable surface-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and non-ionic compounds.

The compositions of the invention may contain linear alkylbenzene sulphonate, particularly linear alkylbenzene sulphonates having an alkyl chain length of $C_8$–$C_{15}$. It is preferred if the level of linear alkylbenzene sulphonate is from 0 wt % to 30 wt %, more preferably 1 wt % to 25 wt %, most preferably from 2 wt % to 15 wt %.

The compositions of the invention may contain other anionic surfactants in amounts additional to the percentages quoted above. Suitable anionic surfactants are well-known to those skilled in the art. Examples include primary and secondary alkyl sulphates, particularly $C_8$–$C_{15}$ primary alkyl sulphates; alkyl ether sulphates; olefin sulphonates; alkyl xylene sulphonates; dialkyl sulphosuccinates; and fatty acid ester sulphonates. Sodium salts are generally preferred.

The compositions of the invention may also contain non-ionic surfactant. Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol.

Non-ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %.

Any conventional fabric conditioning agent may be used in the compositions of the present invention. The conditioning agents may be cationic or non-ionic. If the fabric conditioning compound is to be employed in a main wash detergent composition the compound will typically be non-ionic. For use in the rinse phase, typically they will be cationic. They may for example be used in amounts from 0.5% to 35%, preferably from 1% to 30% more preferably from 3% to 25% by weight of the composition.

Suitable cationic fabric softening compounds are substantially water-insoluble quaternary ammonium materials comprising a single alkyl or alkenyl long chain having an average chain length greater than or equal to $C_{20}$ or, more preferably, compounds comprising a polar head group and two alkyl or alkenyl chains having an average chain length greater than or equal to $C_{14}$. Preferably the fabric softening compounds have two long chain alkyl or alkenyl chains each having an average chain length greater than or equal to $C_{16}$. Most preferably at least 50% of the long chain alkyl or alkenyl groups have a chain length of $C_{18}$ or above. It is preferred if the long chain alkyl or alkenyl groups of the fabric softening compound are predominantly linear.

Quaternary ammonium compounds having two long-chain aliphatic groups, for example, distearyldimethyl ammonium chloride and di(hardened tallow alkyl) dimethyl ammonium chloride, are widely used in commercially available rinse conditioner compositions. Other examples of these cationic compounds are to be found in "Surfactants Science Series" volume 34 ed. Richmond 1990, volume 37 ed. Rubingh 1991 and volume 53 eds. Cross and Singer 1994, Marcel Dekker Inc. New York".

Any of the conventional types of such compounds may be used in the compositions of the present invention.

The fabric softening compounds are preferably compounds that provide excellent softening, and are characterised by a chain melting $L_\beta$ to $L_\alpha$ transition temperature greater than 25° C., preferably greater than 35° C., most preferably greater than 45° C. This $L_\beta$ to $L_\alpha$ transition can be measured by differential scanning calorimetry as defined in "Handbook of Lipid Bilayers", D Marsh, CRC Press, Boca Raton, Fla., 1990 (pages 137 and 337).

Substantially water-insoluble fabric softening compounds are defined as fabric softening compounds having a solubility of less than $1\times10^{-3}$ wt % in demineralised water at 20° C. Preferably the fabric softening compounds have a solubility of less than $1\times10^{-4}$ wt %, more preferably less than $1\times10^{-8}$ to $1\times10^{-6}$ wt %.

Especially preferred are cationic fabric softening compounds that are water-insoluble quaternary ammonium materials having two $C_{12-22}$ alkyl or alkenyl groups connected to the molecule via at least one ester link, preferably two ester links. An especially preferred ester-linked quaternary ammonium material can be represented by the formula:

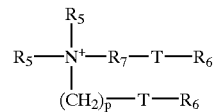

wherein each $R_5$ group is independently selected from $C_{1-4}$ alkyl or hydroxyalkyl groups or $C_{2-4}$ alkenyl groups; each $R_6$ group is independently selected from $C_{8-28}$ alkyl or alkenyl groups; and wherein $R_7$ is a linear or branched alkylene group of 1 to 5 carbon atoms, T is

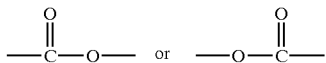

and p is 0 or is an integer from 1 to 5.

Di(tallowoxyloxyethyl) dimethyl ammonium chloride and/or its hardened tallow analogue is an especially preferred compound of this formula.

A second preferred type of quaternary ammonium material can be represented by the formula:

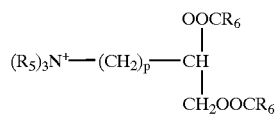

wherein $R_5$, p and $R_6$ are as defined above.

A third preferred type of quaternary ammonium material are those derived from triethanolamine (hereinafter referred to as 'TEA quats') as described in for example U.S. Pat. No. 3,915,867 and represented by formula:

wherein T is H or ($R_8$—CO—) where $R_8$ group is independently selected from $C_{8-28}$ alkyl or alkenyl groups and $R_9$ is $C_{1-4}$ alkyl or hydroxyalkyl groups or $C_{2-4}$ alkenyl groups. For example N-methyl-N,N, N-triethanolamine ditallowester or di-hardened-tallowester quaternary ammonium chloride or methosulphate. Examples of commercially available TEA quats include Rewoquat WE18 and Rewoquat WE20, both partially unsaturated (ex. WITCO), Tetranyl AOT-1, fully saturated (ex. KAO) and Stepantex VP 85, fully saturated (ex. Stepan).

It is advantageous if the quaternary ammonium material is biologically biodegradable.

Preferred materials of this class such as 1,2-bis(hardened tallowoyloxy)-3-trimethylammonium propane chloride and their methods of preparation are, for example, described in U.S. Pat. No. 4,137,180 (Lever Brothers Co). Preferably these materials comprise small amounts of the corresponding monoester as described in U.S. Pat. No. 4,137,180, for example, 1-hardened tallowoyloxy-2-hydroxy-3-trimethylammonium propane chloride.

Other useful cationic softening agents are alkyl pyridinium salts and substituted imidazoline species. Also useful are primary, secondary and tertiary amines and the condensation products of fatty acids with alkylpolyamines.

The compositions may alternatively or additionally contain water-soluble cationic fabric softeners, as described in GB 2 039 556B (Unilever).

The compositions may comprise a cationic fabric softening compound and an oil, for example as disclosed in EP-A-0829531.

The compositions may alternatively or additionally contain nonionic fabric softening agents such as lanolin and derivatives thereof.

Lecithins and other phospholipids are also suitable softening compounds.

In fabric softening compositions nonionic stabilising agent may be present. Suitable nonionic stabilising agents may be present such as linear $C_8$ to $C_{22}$ alcohols alkoxylated with 10 to 20 moles of alkylene oxide, $C_{10}$ to $C_{20}$ alcohols, or mixtures thereof. Other stabilising agents include the deflocculating polymers as described in EP 0415698A2 and EP 0458599 B1.

Advantageously the nonionic stabilising agent is a linear $C_8$ to $C_{22}$ alcohol alkoxylated with 10 to 20 moles of alkylene oxide. Preferably, the level of nonionic stabiliser is within the range from 0.1 to 10% by weight, more preferably from 0.5 to 5% by weight, most preferably from 1 to 4% by weight. The mole ratio of the quaternary ammonium compound and/or other cationic softening agent to the nonionic stabilising agent is suitably within the range from 40:1 to about 1:1, preferably within the range from 18:1 to about 3:1.

The composition can also contain fatty acids, for example $C_8$ to $C_{24}$ alkyl or alkenyl monocarboxylic acids or polymers thereof. Preferably saturated fatty acids are used, in particular, hardened tallow $C_{16}$ to $C_{18}$ fatty acids. Preferably the fatty acid is non-saponified, more preferably the fatty acid is free, for example oleic acid, lauric acid or tallow fatty acid. The level of fatty acid material is preferably more than 0.1% by weight, more preferably more than 0.2% by weight. Concentrated compositions may comprise from 0.5 to 20% by weight of fatty acid, more preferably 1% to 10% by weight. The weight ratio of quaternary ammonium material or other cationic softening agent to fatty acid material is preferably from 10:1 to 1:10.

It is also possible to include certain mono-alkyl cationic surfactants which can be used in main-wash compositions for fabrics. Cationic surfactants that may be used include quaternary ammonium salts of the general formula $R_1R_2R_3R_4N^+X^-$ wherein the R groups are long or short hydrocarbon chains, typically alkyl, hydroxyalkyl or ethoxylated alkyl groups, and X is a counter-ion (for example, compounds in which $R_1$ is a $C_8$–$C_{22}$ alkyl group, preferably a $C_8$–$C_{10}$ or $C_{12}$–$C_{14}$ alkyl group, $R_2$ is a methyl group, and $R_3$ and $R_4$, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60 wt %, for example, in a composition for washing fabrics by hand. In compositions for machine washing of fabrics, an amount of from 5 to 40 wt % is generally appropriate. Typically the compositions will comprise at least 2 wt % surfactant e.g. 2–60%, preferably 15–40% most preferably 25–35%.

Detergent compositions suitable for use in most automatic fabric washing machines generally contain anionic non-soap surfactant, or non-ionic surfactant, or combinations of the two in any suitable ratio, optionally together with soap.

The compositions of the invention, when used as main wash fabric washing compositions, will generally also contain one or more detergency builders. The total amount of detergency builder in the compositions will typically range from 5 to 80 wt %, preferably from 10 to 60 wt %.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202

(Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50 wt %.

The alkali metal aluminosilicate may be either crystalline or amorphous or mixtures thereof, having the general formula: 0.8–1.5 $Na_2O$ $Al_2O_3$. 0.8–6 $SiO_2$ These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20.

Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di and trisuccinates, carboxymethyloxy succinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N',-tetracetyl ethylenediamine (TAED) and sodium nonanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. examples of such peracids can be found in U.S. Pat. No. 4,686,063 and U.S. Pat. No. 5,397,501 (Unilever). A preferred example is the imido peroxycarboxylic class of peracids described in EP A 325 288, EP A 349 940, DE 382 3172 and EP 325 289. A particularly preferred example is phthalimido peroxy caproic acid (PAP). Such peracids are suitably present at 0.1–12%, preferably 0.5–10%.

A bleach stabiliser (transition metal sequestrant) may also be present. Suitable bleach stabilisers include ethylenediamine tetra-acetate (EDTA), the polyphosphonates such as Dequest (Trade Mark) and non-phosphate stabilisers such as EDDS (ethylene diamine di-succinic acid). These bleach stabilisers are also useful for stain removal especially in products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

The compositions according to the invention may also contain one or more enzyme(s). Suitable enzymes include the proteases, amylases, cellulases, oxidases, peroxidases and lipases usable for incorporation in detergent compositions. Preferred proteolytic enzymes (proteases) are, catalytically active protein materials which degrade or alter protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4–12 are available and can be used in the instant invention. Examples of suitable proteolytic enzymes are the subtilisins which are obtained from particular strains of *B. Subtilis B. licheniformis*, such as the commercially available subtilisins Maxatase (Trade Mark), as supplied by Genencor International N.V., Delft, Holland, and Alcalase (Trade Mark), as supplied by Novozymes Industri A/S, Copenhagen, Denmark.

Particularly suitable is a protease obtained from a strain of Bacillus having maximum activity throughout the pH range of 8–12, being commercially available, e.g. from Novozymes Industri A/S under the registered trade-names Esperase (Trade Mark) and Savinase (Trade-Mark). The preparation of these and analogous enzymes is described in GB 1 243 785. Other commercial proteases are Kazusase (Trade Mark obtainable from Showa-Denko of Japan), Optimase (Trade Mark from Miles Kali-Chemie, Hannover, West Germany), and Superase (Trade Mark obtainable from Pfizer of U.S.A.).

Detergency enzymes are commonly employed in granular form in amounts of from about 0.1 to about 3.0 wt %. However, any suitable physical form of enzyme may be used.

The compositions of the invention may contain alkali metal, preferably sodium carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate copolymer, or sodium silicate. One preferred powder structurant is fatty acid soap, suitably present in an amount of from 1 to 5 wt %.

Other materials that may be present in detergent compositions of the invention include sodium silicate; antiredeposition agents such as cellulosic polymers; soil release polymers; inorganic salts such as sodium sulphate; or lather boosters as appropriate; proteolytic and lipolytic enzymes; dyes; coloured speckles; fluorescers and decoupling polymers. This list is not intended to be exhaustive. However, many of these ingredients will be better delivered as benefit agent groups in materials according to the first aspect of the invention.

The detergent composition when diluted in the wash liquor (during a typical wash cycle) will typically give a pH of the wash liquor from 7 to 10.5 for a main wash detergent.

Particulate detergent compositions are suitably prepared by spray-drying a slurry of compatible heat-insensitive ingredients, and then spraying on or post-dosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l. Especially preferred compositions have bulk densities of at least 650 g/liter, more preferably at least 700 g/liter.

Such powders may be prepared either by post-tower densification of spray-dried powder, or by wholly non-tower methods such as dry mixing and granulation; in both cases a high-speed mixer/granulator may advantageously be used. Processes using high-speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

Substrate

The substrate may be any substrate onto which it is desirable to deposit silicones and which is subjected to treatment such as a washing or rinsing process.

In particular, the substrate may be a textile fabric, fabric, preferably of cotton.

It has been found that particular good results are achieved when using a natural fabric substrate such as cotton, or fabric blends containing cotton.

Treatment

The treatment of the substrate with the material of the invention can be made by any suitable method such as washing, soaking or rinsing of the substrate.

Typically the treatment will involve a washing or rinsing method such as treatment in the main wash or rinse cycle of a washing machine and involves contacting the substrate with an aqueous medium comprising the material of the invention.

The present invention will now be explained in more detail by reference to the following non-limiting examples:—

In the following examples where percentages are metioned, this is to be understood as percentage by weight. In the following tables where the values do not add up to 100 these are to be understood as parts by weight.

EXAMPLE 1

Sample Synthesis of an Ester Linked Cellulose Monoacetate (CMA) Silicone

Monocarboxydecyl terminated polydimethylsiloxane (PDMS) source (Mwt 5,000: 1.5 g, 0.23 mmols) was dispersed in dimethylacetamide (10 cm$^3$) by vigorous stirring under nitrogen. Carbonyldiimidazole (37 mg, 0.23 mmols) was then added and the dispersion heated with stirring to 70° C. under nitrogen for two hours. A solution of cellulose monoacetate (DS 0.58; 1 g, 5.3 mmol equivalents based on primary hydroxyl groups) in dimethylacetamide (10 cm$^3$) was then added and stirring and heating was continued for a further 20 hours. Following this time the mixture was filtered and the filtrate added to vigorously stirring acetone to give a white precipitate. This precipitate was filtered off, washed with acetone and dried under vacuum to give a white polymer (1.01 g). From the $^1$H NMR of the polymer (after hydrolysis of 20% DCl in D$_2$O for two hours at 80° C.) and normalising the integration of the anomeric protons to unity and the acetate group to 0.58 the Si—CH$_3$ group (at 0.0 ppm) integration gives an overall degree of substitution (DS) of siloxane group as 0.04.

EXAMPLE 2

Preparation of PDMS-Grafted Cellulose Monoacetate Attachment of PDMS Via a Carbonate Linkage Carbinol (hydroxyl) terminated PDMS (Mwt 5,000; 11.5 g, 2.3 mmol) was dispersed in anhydrous dimethylacetamide (20 cm$^3$) with % of a sodium hydroxide pellet. The solution was stirred with heating (60° C.) under nitrogen for 30 mins prior to the addition of 1,1'-carbonyldiimidazole (0.74 g, 4.6 mmols). After two hours a solution of cellulose monoacetate (10 g) in dimethylacetamide (100 cm$^3$) was added and stirring the heating was continued for a further 18 hours. The solution was then allowed to cool at room temperature and added slowly to vigorously stirring acetone (500 cm$^3$) to give a light brown precipitate, the polymer was filtered off and washed with acetate by continuous extraction for 18 hours. Finally, the polymer was dried under vacuum at 40° C. for 18 hours to give a light tan solid (3.87 g). From the $^1$H NMR of the polymer (after hydrolysis in 20% DCl in D$_2$O for an hour at 80° C.) and normalising the integration of the anomeric protons to unity and the acetate group to 0.58 the Si—CH$_3$ group (at 0.0 ppm) integration gives an overall DS of the PDMS group as 0.0063.

EXAMPLE 3

Preparation of PDMS-Grafted Cellulose Monoacetate Attachment of PDMS Via a Carbamate Linkage Cellulose monoacetate (10 g) was dissolved in anhydrous dimethylacetamide (100 Cm$^3$) with stirring and heating (60° C.) under nitrogen, 1,1'-carbonyldiimidazole (0.74 g, 4.6 mmols) and ¼ of a sodium hydroxide was then added and the solution was stirred and heated for a further 2 hours. A solution of aminopropyl terminated PDMS (Mwt 1,000; 6.9 g. 6.0 mmols) in dimethylacetamide (50 cm$^3$) was then added and the solution was stirred with heating for a further 18 hours. The resulting slurry was then centrifuged and the supernatant added dropwise the vigorously stirring acetone (500 cm$^3$) to give an off-white polymer. The precipitate was filtered off, washed with acetone (300 cm$^3$) and dried under vacuum (40° C.) to give a tan-coloured solid (2.2 g). From the $^1$H NMR of the polymer (after hydrolysis in 20% DCl in D$_2$O for an hour at 80° C.) and normalising the integration of the anomeric protons to unity and the acetate group to 0.58 the Si—CH$_3$ group (at 0.0 ppm) integration gives an overall DS of the PDMS group as 0.039.

EXAMPLE 4

Use of CMA-Silicone in a Detergent Formulation to Give a Fabric Cares Benefit Formulations

| Ingredient | Quantity/Parts by Weight | |
|---|---|---|
| | Example | Control A |
| NaLAS | 20.9 | 20.9 |
| C$_{12-15}$ 7EO alcohol ethoxylate | 20.9 | 20.9 |
| Sodium Carbonate | 31.3 | 31.3 |
| Sodium Bicarbonate | 10.2 | 10.2 |
| Polymer A | 16.7 | — |
| Polymer B | — | 16.7 |

Polymer A is the modified cellulose acetate with grafted polymethylsiloxane described in example 1.
Polymer B is a cellulose acetate having a molecular weight of 16200 and a degree of substitution of 0.58, without polydimethylsilixone graft.

Wash liquors were prepared at 40° C. in each of two Rotawash pots consisting of 200 cm$^3$ of water (16° French Hard) to which had been added, 0.478 g of either the Example formulation or the control formulation A. To each pot was also added one piece (20 cm×20 cm) of white mercerised woven cotton and one piece (20 cm×20 cm) of a similar cotton dyed at a 1% level with Direct Red 80. The fabrics were washed for 30 minutes at 40° C. using a standard agitation rate of 40 rpm. At the end of the wash, each set of fabrics was rinsed with 2 changes of 1000 cm$^3$ of water (20° C., 16° French Hard). The fabric sets were air-dried at ambient temperature and then each set was subjected to the same wash procedure up to five times. After drying for the fifth wash the "white" cloths from each wash condition were then stored in a humidity-controlled room (65° C. Humidity 23° C. Temperature) for 24 hrs to equilibrate. After this time the cloths were measured on the Kawabata Shear machine, to obtain shear hysterisis parameters as the 2HG5 values. This value is a measure of the lubricity between fibres and yarns of the fabric and has been correlated to both softness and crease reduction(REF: The use of Kawabata Instrumentation to evaluate Silicone fabric softeners by A. J. Sabia and A. M. Pagliuchi). The lower the 2HG5 value the greater the softness of the fabric.

| | Kawabata 2HG5 results | |
|---|---|---|
| | Example Formulation | Control Formulation |
| White cloth from wash 5 | 6.15 | 6.83 |

FORMULATION EXAMPLES

Examples 5–8 are formulation examples. In each case "Polymer A" refers, respectively, to the materials specified in Examples 1 or 2.

Raw Material Specification:

| Component | Specification |
|---|---|
| LAS | Alkyl Benzene Sulphonic-acid, Marlon AS3, ex Huls |
| Na-PAS | Primary Alkyl Benzene Sulphonic-acid, neutralised with NaOH |
| Dobanol 25-7 | C$_{12-15}$ ethoxylated alcohol, 7EO, ex shell |
| Zeolite | Wassalith P, ex Degussa |
| STPP | Sodium Tri Polyphosphate, Thermphos NW, ex Hoechst |
| Dequest 2066 | Metal chelating agent, ex Monsanto |
| Lipolase | Type 100L, ex Novo |
| Savinase 16L | Protease, ex Novo |
| Sokalan CP5 | Acrylic/Maleic Builder Polymer, ex BASF |
| Defloculating Polymer | Polymer A-11 disclosed in EP-A-346 995 |
| SCMC | Sodium Carboxymethyl Cellulose |
| Minors | Antiredeposition polymers, transition-matal scavangers/bleach stabilisers, fluorescers, dye-transfer-inhibition polymers, enzymes, |
| Polymer A | Material Specified in Example 1. |

EXAMPLE 5

Spray-Dried Powder

| Component | % w/w |
|---|---|
| Na PAS | 11.5 |
| Dobanol 25-7 | 6.3 |
| Soap | 2 |
| Zeolite | 24.1 |
| SCMC | 0.6 |
| Na Citrate | 10.6 |
| Na Carbonate | 23 |
| Polymer A | 0.3 |
| Dequest 2066 | 0.4 |
| Sokalan CP5 | 0.9 |
| Savinase 16L | 0.7 |
| Lipolase | 0.1 |
| Minors | 0.4 |
| Water/salts | Up to 100% |

EXAMPLE 6
Detergent Granulate Prepared by Non-Spray Drying Method

| Component | % w/w |
| --- | --- |
| Na PAS | 13.5 |
| Dobanol 25-7 | 2.5 |
| STPP | 45.3 |
| Na Carbonate | 4 |
| Polymer A | 0.28 |
| Na Silicate | 10.1 |
| Minors | 1.5 |
| Water | Up to 100% |

EXAMPLE 7
Isotropic Laundry Liquid

| Component | % w/w |
| --- | --- |
| Na Citrate | 10.7 |
| Propylene Glycol | 7.5 |
| Ethylene Glycol | 4.5 |
| Borax | 3 |
| Savinase 16L | 0.3 |
| Lipolase | 0.1 |
| Polymer A | 0.25 |
| Monoethanolamine | 0.5 |
| Coco fatty acid | 1.7 |
| NaOH (50%) | 2.2 |
| LAS | 10.3 |
| Dobanol 25-7 | 6.3 |
| LES | 7.6 |
| Minors | 1.3 |
| (adjust pH to 7 white NaOH) | |
| Water | Up to 100% |

EXAMPLE 8
Structured Laundry Liquids

| Component | % w/w |
| --- | --- |
| LAS | 16.5 |
| Dobanol 25-7 | 9 |
| Oleic acid (Priolene (6907)) | 4.5 |
| Zeolite | 15 |
| KOH, neutralisation of acids and pH to 8.5 | |
| Citric acid | 8.2 |
| Deflocculating Polymer | 1 |
| Protease | 0.38 |
| Lipolase | 0.2 |
| Polymer A | 0.15 |
| Minors | 0.4 |
| Water | Up to 100% |

We claim:

1. A substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains;

wherein the silicone chain(s) is or are independently selected from those of formula:

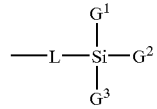

wherein L is absent or is a linking group and one or two of substituents $G^1$–$G^3$ is a methyl group, the remainder being selected from groups of formula

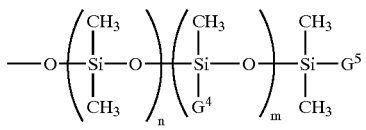

the —Si(CH$_3$)$_2$O— groups and the —Si(CH$_3$O)(G$^4$)- groups being arranged in random or block fashion;

wherein n is from 5 to 1000, and m is from 0 to 100, $G^4$ is selected from groups of formula:

—(CH$_2$)$_p$—CH$_3$, where p is from 1 to 18

—(CH$_2$)$_q$—NH—(CH$_2$)$_r$—NH$_2$ where q and r are independently from 1 to 3

—(CH$_2$)$_s$—NH$_2$, where s is from 1 to 3

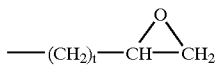

where t is from 1 to 3

—(CH$_2$)$_u$—COOH, where u is from 1 to 10,

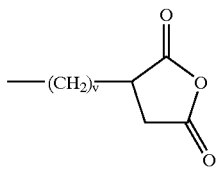

where v is from 1 to 10, and

—(CH$_2$CH$_2$O)$_w$—(CH$_2$)$_x$H, where w is from 1 to 150, and x is from 0 to 10;

and $G^5$ is independently selected from hydrogen, groups defined above for $G^4$, —OH, —CH$_3$ and —C(CH$_3$)$_3$.

2. The substituted polysaccharide of claim 1, wherein the average degree of substitution of the silicone chain(s) is from 0.001 to 0.5.

3. The substituted polysaccharide of claim 1 wherein the substituted polysaccharide comprises only $\beta_{1-4}$ linkages.

4. The substituted polysaccharide of claim 1 wherein the substituted polysaccharide comprises additional linkages.

5. The substituted polysaccharide of claim 4 wherein the substituted polysaccharide comprises $\beta_{1-4}$ and $\beta_{1-3}$ linkages.

6. The substituted polysaccharide of claim 5 wherein the weight ratio of $\beta_{1-3}$ and $\beta_{1-4}$ linkages is from 1:100 to 1:2.

7. The substituted polysaccharide of claim 1, where L is selected from the group consisting of amide linkages, ester linkages, ether linkages, urethane linkages, triazine linkages, carbonate linkages, amine linkages and ester-alkylene linkages.

8. The substituted polysaccharide of claim 1, wherein the chemical change is hydrolysis, perhydrolysis or bond-cleavage.

9. The substituted polysaccharide of claim 1, wherein the group(s) which undergo the chemical change comprise one or more groups attached via an ester linkage to the polysaccharide.

10. The substituted polysaccharide of claim 1, having the general formula (1):

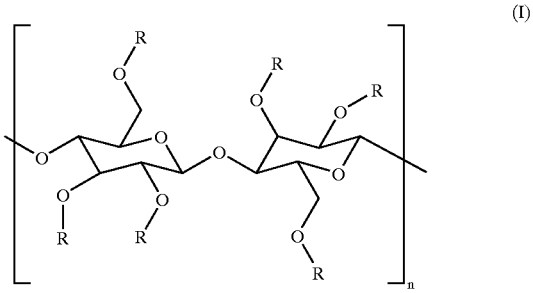

wherein at least one or more —OR groups of the polymer are independently substituted or replaced by silicone chains and at least one or more R groups are independently selected from groups of formulae:

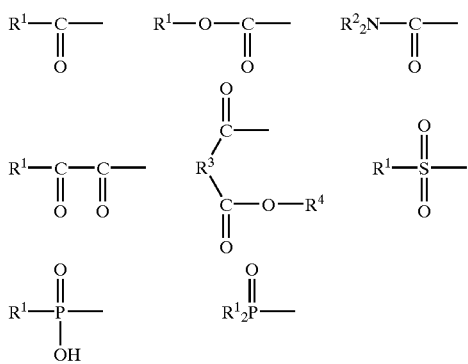

wherein each $R^1$ is independently selected from $C_{1-20}$ alkyl, $C_{2-20}$ alkenyl and $C_{5-7}$ aryl any of which is optionally substituted by one or more substituents independently selected from $C_{1-4}$ alkyl, $C_{1-12}$ alkoxy, hydroxyl, vinyl and phenyl groups;
each $R^2$ is independently selected from hydrogen and groups $R^1$ as hereinbefore defined;
$R^3$ is a bond or is selected from $C_{1-4}$ alkylene, $C_{2-4}$ alkenylene and $C_{5-7}$ arylene groups, the carbon atoms in any of these being optionally substituted by one or more substituents independently selected from $C_{1-12}$ alkoxy, vinyl, hydroxyl, halo and amine groups;
each $R^4$ is independently selected from hydrogen, counter cations, and groups $R^1$ as hereinbefore defined;
groups R which together with the oxygen atom forming the linkage to the respective saccharide ring forms an ester or hemi-ester group of a tricarboxylic- or higher polycarboxylic- or other complex acid selected from the group consisting of citric acid, an amino acid, or a combination thereof;
and n is the number of repeat units in the polysaccharide and is selected so that the number average molecular weight of the polysaccharide is in the range of 1,000 to 200,000.

11. The substituted polysaccharide of claim 9 wherein the ester-linked group(s) is/are selected from carboxylic acid esters.

12. The substituted polyssaccharide of claims 9, wherein the ester-linked group(s) is/are independently selected from one or more of acetate, propanoate, trifluroacetate, 2-(2-hydroxy-1-oxopropoxy) propanoate, lactate, glycolate, pyruvate, crotonate, isovalerate, cinnamate, formate, salicylate, carbamate, methylcarbamate, benzoate, gluconate, methanesulphonate, toluene sulphonate, groups and hemiester groups of fumaric, malonic, itaconic, oxalic, maleic, succinic, tartaric, aspartic, glutamic, and malic acids.

13. The substituted polysaccharide of claim 1, wherein the average degree of substitution on the saccharide rings of the groups which undergo the chemical change is from 0.1 to 3.

14. A method of depositing a silicone onto a substrate, the method comprising contacting in an aqueous solution, the substrate and a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains; and wherein the silicone chain(s) is or are independently selected from those of formula:

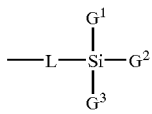

wherein L is absent or is a linking group and one or two of substituents $G^1$–$G^3$ is a methyl group, the remainder being selected from groups of formula

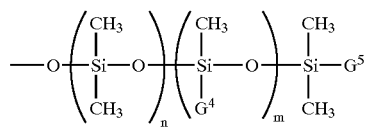

the —Si(CH$_3$)$_2$O— groups and the —Si(CH$_3$O)(G$^4$)- groups being arranged in random or block fashion;
wherein n is from 5 to 1000, and m is from 0 to 100,
$G^4$ is selected from groups of formula:
—(CH$_2$)$_p$—CH$_3$, where p is from 1 to 18
—(CH$_2$)$_q$—NH—(CH$_2$)$_r$—NH$_2$ where q and r are independently from 1 to 3
—(CH$_2$)$_s$—NH$_2$, where s is from 1 to 3

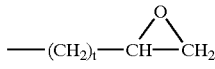

where t is from 1 to 3
—(CH$_2$)$_u$—COOH, where u is from 1 to 10,

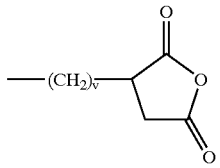

where v is from 1 to 10, and
—(CH$_2$CH$_2$O)$_w$—(CH$_2$)$_x$H, where w is from 1 to 150, and x is from 0 to 10;
and $G^5$ is independently selected from hydrogen, groups defined above for $G^4$, —OH, —CH$_3$ and —C(CH$_3$)$_3$.

15. A composition comprising a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains and at least one further component; and wherein the silicone chain(s) is or are independently selected from those of formula:

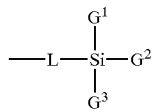

wherein L is absent or is a linking group and one or two of substituents $G^1$–$G^3$ is a methyl group, the remainder being selected from groups of formula

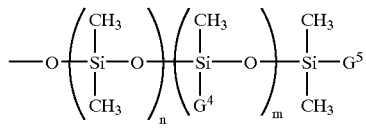

the —Si(CH$_3$)$_2$O— groups and the —Si(CH$_3$O)(G$^4$)- groups being arranged in random or block fashion;
wherein n is from 5 to 1000, and m is from 0 to 100, $G^4$ is selected from groups of formula:
—(CH$_2$)$_p$—CH$_3$, where p is from 1 to 18
—(CH$_2$)$_q$—NH—(CH$_2$)$_r$—NH$_2$ where q and r are independently from 1 to 3
—(CH$_2$)$_s$—NH$_2$, where s is from 1 to 3

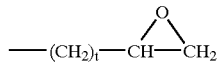

where t is from 1 to 3
—(CH$_2$)$_u$—COOH, where u is from 1 to 10,

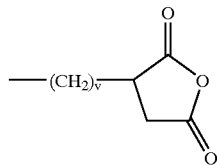

where v is from 1 to 10, and
—(CH$_2$ CH$_2$O)$_w$—(CH$_2$)$_x$H, where w is from 1 to 150, and x is from 0 to 10;
and $G^5$ is independently selected from hydrogen, groups defined above for $G^4$, —OH, —CH$_3$ and —C(CH$_3$)$_3$.

16. A composition of claim 15, in which the further component comprises a surfactant.

17. The composition of claim 15, comprising from 0.01% to 25%, by weight of the substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains.

18. A method of enhancing the softening benefit of the composition on a substrate, the method comprising the application of a substituted polysaccharide comprising $\beta_{1-4}$ linkages having covalently bonded on the polysaccharide moiety thereof, at least one deposition enhancing group which undergoes a chemical change in water at a use temperature to increase the affinity of the substituted polysaccharide to a substrate, the substituted polysaccharide further comprising one or more independently selected silicone chains, onto a substrate; and wherein the silicone chain(s) is or are independently selected from those of formula:

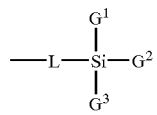

wherein L is absent or is a linking group and one or two of substituents $G^1$–$G^3$ is a methyl group, the remainder being selected from groups of formula

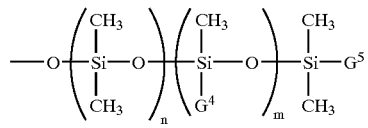

the —Si(CH$_3$)$_2$O— groups and the —Si(CH$_3$O)(G$^4$)- groups being arranged in random or block fashion;
wherein n is from 5 to 1000, and m is from 0 to 100, $G^4$ is selected from groups of formula:
—(CH$_2$)$_p$—CH$_3$, where p is from 1 to 18
—(CH$_2$)$_q$—NH—(CH$_2$)$_r$—NH$_2$ where q and r are independently from 1 to 3
—(CH$_2$)$_s$—NH$_2$, where s is from 1 to 3

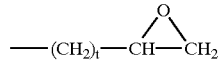

where t is from 1 to 3
—(CH$_2$)$_u$—COOH, where u is from 1 to 10,

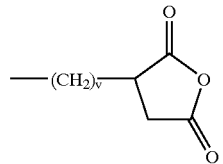

where v is from 1 to 10, and
—(CH$_2$ CH$_2$O)$_w$—(CH$_2$)$_x$H, where w is from 1 to 150, and x from 0 to 10;
and $G^5$ is independently selected from hydrogen, groups defined above for $G^4$, —OH, —CH$_3$ and —C(CH$_3$)$_3$.

19. The substituted polysaccharide of claim 1 where w is from 10 to 20.

20. The method of claim 14 where w is from 10 to 20.

21. The method of claim 15 where w is from 10 to 20.

22. The method of claim 18 where w is from 10 to 20.

* * * * *